United States Patent [19]

Osbon et al.

[11] Patent Number: 5,306,227
[45] Date of Patent: Apr. 26, 1994

[54] APPARATUS FOR AUGMENTING MALE POTENCY

[75] Inventors: Robert E. Osbon, Taylors, S.C.; James B. Osbon, Richmond, Va.

[73] Assignee: Osbon Medical Systems, Ltd., Augusta, Ga.

[21] Appl. No.: 883,083

[22] Filed: May 15, 1992

Related U.S. Application Data

[63] Continuation-in-part of Ser. No. 880,308, May 5, 1992, abandoned, which is a continuation of Ser. No. 504,354, Apr. 3, 1990, abandoned, and a continuation of Ser. No. 820,216, Jan. 10, 1992, Pat. No. D. 343,455.

[51] Int. Cl.⁵ .............................................. A61F 5/00
[52] U.S. Cl. ..................................................... 600/41
[58] Field of Search .............................. 600/38, 39, 41

[56] References Cited

U.S. PATENT DOCUMENTS

| D. 293,473 | 12/1987 | Chaney . | |
|---|---|---|---|
| D. 317,504 | 6/1991 | Osbon . | |
| D. 317,505 | 6/1991 | Osbon . | |
| 594,815 | 11/1897 | Taggart . | |
| 2,581,114 | 1/1952 | Larson . | |
| 2,818,855 | 1/1958 | Miller | 600/41 |
| 3,461,863 | 8/1969 | Sullinger . | |
| 3,759,253 | 9/1973 | Cray . | |
| 4,203,432 | 5/1980 | Koch . | |
| 4,378,008 | 3/1983 | Osbon, Sr. . | |
| 4,539,980 | 9/1985 | Chaney . | |
| 4,628,915 | 12/1986 | Chaney . | |
| 4,753,227 | 6/1988 | Yanuck, Jr. . | |
| 4,856,498 | 8/1989 | Osbon . | |

OTHER PUBLICATIONS

James E. Crouch, Functional Human Anatomy, pp. 436, 446, 447; 1972; Philadelphia.

Primary Examiner—Cary E. O'Connor
Attorney, Agent, or Firm—Dority & Manning

[57] ABSTRACT

The construction of an integral cincture band of elastic material may include a pair of semi-ellipsoidal handles and an enlarged region to be aligned with the urethra of the user's male sex organ so as to relatively reduce the urethral constriction for improved seminal fluid discharge. Radially inwardly projecting regions of predetermined radius of curvature which is relatively large to the overall ring may be provided in predetermined circumferential locations on each lateral side of the dorsal centerline. By such arrangement, effective pressure is applied to the subcutaneous lateral veins and generally to the dorsal venous process of the penis without direct application of constrictive force to the center of the penis dorsal area, thereby minimizing user pressure discomfort or loss of sensation. Relatively inelastic material, such as spherical elements of hardened plastic, may be included in the inwardly projecting regions to further enhance specific circumferentially located blood flow restriction pressures.

32 Claims, 3 Drawing Sheets

APPARATUS FOR AUGMENTING MALE POTENCY

BACKGROUND AND SUMMARY OF THE INVENTION

This application is a continuation-in-part of copending application U.S. Ser. No. 07/880,308 filed May 5, 1992, now abandoned, and entitled "Improved Apparatus For Augmenting Male Potency," which is a file wrapper continuation of prior application U.S. Ser. No. 07/504,354 filed on Apr. 3, 1990, and abandoned on the filing of such file wrapper continuation. This application is also a continuation of copending U.S. Ser. No. 07/820,216, filed on Jan. 10, 1992 now U.S. Pat. No. D 343,455. To the extent applicable, priority is hereby claimed under 35 U.S.C. Section 120 to all such earlier filed applications.

The present invention deals in general with improved apparatus for augmenting male potency, and in particular concerns certain improvements in cincture band construction, such as for use in conjunction with vacuum tumescence enhancement therapies using, for example, a generally cylindrical vacuum chamber.

Vacuum generating devices for augmenting male potency which evacuate a cylinder placed over the male organ, and thereby induce engorgement, are generally known. Likewise, the use of cincture bands or other resilient members to retain such engorgement are also known. See for example U.S. Pat. No. 4,856,498 issued to Osbon, commonly assigned with this application, and entitled "Vacuum Generating And Constriction Apparatus For Augmenting Male Potency." In general, evacuation of the cylinder (once received over the male sex organ) draws blood into the organ so that the flaccid penis becomes erect for sexual intercourse. A constriction device applied to the base or root of the male sex organ operates to retain the erect condition through garroting or cincturing the blood drawn into the engorged organ.

While the foregoing basic operations and related methodology are well-known and to a certain degree effective as one therapeutic approach to male impotence, improvements have been sought in specific operations such as manipulation and use of the various apparatuses. For example, manipulation of resilient cincture bands typically involves expansion of the resilient band and subsequent placement thereof onto the root of the male sex organ. Chaney, U.S. Pat. No. 4,628,915, discloses a cone-like accessory device and associated latchable sleeve. The cone is used to expand an elastic ring onto a sleeve. Thereafter, the sleeve is unlatched from the cone and slipped onto the base of the male sex organ for transfer of the elastic ring thereto. Blood is subsequently massaged into the male sex organ where it is retained by the seated elastic ring.

Prior art devices have often made use of plain circular members for cincturing operations. See for example U.S. Pat. Nos. 3,461,863 to Sullinger; 4,378,008 to Osbon, Sr.; and 4,753,227 to Yanuck, Jr. While such plain or circular members perform adequately in certain respects, improvements have been sought. For example, the above-referenced, commonly assigned U.S. Pat. No. 4,856,498 to Osbon discloses a toroidal shaped elastic ring with specialized handle members to faciliate manipulation of the ring and its use with a vacuum cylinder during a subsequent vacuum cycle or "re-pump." i.e., subsequent vacuum therapy after seating of the ring on the base of an at least partially erect organ, for increased erection size and/or firmness.

Chaney U.S. Pat. Nos. 4,539,980; 4,628,915; and Des. 293,473 all disclose plain circular rings with some form or number of added handle elements.

Other elastic cincture band devices have sought improvement through higher degrees of elaboration and complexity. For example, Cray, U.S. Pat. No. 3,759,253, with an invention entitled "Human Male Appliance," seeks to restrict the flow of blood from the penis while not materially impeding blood flow to the penis. Cray's structural arrangement of a relatively thick appliance with separate opposed pairs of ribs and rib-like members seeks to anatomically reduce blood egress from the penis while permitting normal blood ingress. Dorsal venal blood flow is restricted by a pair of curved ribs 26 and 28 which are about 0.59 inches (15 mm) long in the direction of the distended penis and which have a radius of curvature of about 0.12 inches (3 mm), which is relatively small in relation to the diameter (22 mm) of the Cray center body portion annular opening. Side tabs 14 and 16 are used to seat the appliance onto a flaccid penis, after which an influx of blood into the penis is induced to be captured therein by the relatively smaller ribs 26 and 28 and relatively larger rib-like members 30 and 32.

Taggart, U.S. Pat. No. 594,815, provides a generally triangular device which makes use of lateral expansion of the penis (as the corpora cavernosa become filled) to mechanically draw a top member downward with the intent of pressuring a dorsal vein so as to retain an engorged condition of the male member. Pressure on the dorsal vein is automatically correlated with, and in proportion to, the degree of lateral expansion. The Taggart triangular device may, for example, comprise a hard rubber or metal element, optionally covered by soft elastic material, or otherwise comprised of partly rigid and partly elastic materials.

Koch, U.S. Pat. No. 4,203,432, uses a split ring of substantially inextensible material to grip about a male sexual organ. Elastic bands are looped a selected number of times about hooks on each respective side of the split ring so as to draw the ring hooks together for applying constriction pressure to the penis. The ring inside diameter has alternating projecting lugs and notches, so that only certain circumferential areas of the penis are compressed.

Larson, U.S. Pat. No. 2,581,114, discloses a device which is (like Koch) first placed around the penis and then tightened, as opposed to being an integral member which is passed over the distal end of the penis and passed to the proximal base thereof (like Cray). In Larson, an elastic tube 1 includes a fastening member 10 which is captured in a socket 7 once tube 1 is looped around the penis. The length is adjusted for particular penis circumference by manually moving element 10 inside tube 1. Another element (metallic ball 9) is similarly adjustably positioned in tube 1 so as to engage the dorsal area of the penis and restrict blood egress from the penis by which an erection is "captured." FIG. 7 shows an alternate slidable member 11 (in place of ball 9) received on the outside of tube 1 and FIG. 8 shows another alternate member 12 for slidable use inside tube 1 (in place of ball 9). A rigid yoke 3 is forced into the tube to define the shape thereof in the area of the urethra and to form the socket 7 necessary for wrapping tube 1 around the penis.

Cray, Koch, Larson, and Taggart each also disclose a urethra cradle or an otherwise formed open area for permitting relatively free egress of seminal fluids. The urethra is the urinary canal. In human males, the urethra also serves as the genital duct for discharge of seminal fluids during climactic expulsion (i.e., ejaculation).

The disclosures of all such U.S. patents are fully incorporated herein by reference.

Some concerns generally about prior art cincturing devices relate to their basic function of acting as a tourniquet applied to living tissue. It will be apparent to those of ordinary skill in the art that there is a constant concern for the safety and health of the impotence patient, i.e., the typical user of cincture band devices and vacuum tumescence enhancement therapy. For example, time limits for wearing cincture bands, such as 20 to 30 minutes, are normally applicable.

In addition to potential problems from excessive application time, excessive applications of force or pressure can cause damage even during normally acceptable wearing times. Such damage could occur due to blood loss (i.e., stoppage), direct pressure bruising, or damage to nerve endings and nerve tissue.

Negative affects might be temporary. For example, loss of nerve sensation or feelings of numbness might quickly dissipate after removal of a cincture band. Even so, loss of sensation during use of a cincture band may significantly detract from the desire to use the therapy or the device.

Aside from the prospect of any actual patient damage or any short-term negative affects, short-term pain (or even simple discomfort) from excessive forces or other cincture band problems can detract the user's attention, thereby lessening enjoyment for both parties. In worst cases, a user is unable to continue with the therapy, and the entire purpose fails (i.e., the patient fails to sustain an erection adequate for intercourse).

Other concerns may relate to potential difficulties in handling the cincture ring. These can occur in several instances. First, a cincture band must be applied to the user. In the case of many typical vacuum therapies, the ring is seated onto an erect organ. The circumference of an enlarged or erect penis is generally larger than the inside diameter of an unstretched cincture band so that the resilient band will tend to constrict the penis when applied thereto. Forces to expand a ring adequately so as to fit over an enlarged penis can be significant. Applying such forces to such an object while trying to maintain a perhaps escaping erection can be not only difficult, but highly detracting of the experience for both partners.

In sum, the positive benefits of the experience are enhanced by the degree to which the therapeutic apparatus permits approximation of a fully natural erection process and intercourse. Conversely, the more cumbersome the apparatus involved, the less satisfying the experience.

In addition to the foregoing concerns for practicality, numerous other needs are based on the individual user's physical and subjective requirements, as well as legitimate concerns for privacy, simplicity, and economy while providing apparatuses effective for producing and retaining the desired sexually potent condition (i.e., penile erection).

The present invention recognizes and addresses various of the foregoing problems, and others, concerning cincture band devices and related vacuum therapy operations for augmenting male potency. Thus, broadly speaking, a principle object of this invention is improved apparatus for augmenting male potency. More particularly, a main concern is providing various improved cincture band arrangements for easy, safe, and effective use in augmenting male potency through the initial production of male sex organ engorgement and subsequent retention of such condition.

It is therefore another object of this invention to provide cincture band apparatus which facilitates the retention of an engorged condition with minimized user pressure discomfort or loss of sensation due to nerve impairment. The more natural the cincture band retention process feels to the user, the less interruption and greater confidence the user will have in the overall therapy. Hence, it is a present object to maximize user confidence (of both intercourse partners) in the overall therapy.

Still further it is an object to provide such improved cincturing devices which are particularly suited for direct application from a vacuum cylinder onto the base of an engorged male sex organ.

Another present object is maximized user comfort from an integrally designed resilient material ring, having various optional features such as handles, a urethra channel, and inward venous pressure regions, while having available optional maximized pressure force features such as separate, relative fixed position, pressure elements of relatively inelastic materials in combination with the resilient ring.

Additional objects and advantages of the invention are set forth in, or will be apparent to those of ordinary skill in the art from, the detailed description which follows. Also, it should be appreciated that modifications and variations to the specifically illustrated and discussed features hereof may be practiced in various embodiments and uses of this invention without departing from the spirit and scope thereof, by virtue of present reference thereto. Such variations may include, but are not limited to, substitution of equivalent means and features or materials for those shown or discussed, and the functional or positional reversal of various parts or features, or the like.

Still further, it is to be understood that different embodiments, as well as different presently preferred embodiments, of the present invention may include various combinations of presently disclosed features or their equivalents (including combinations thereof not expressly shown or stated). One exemplary such embodiment of the present invention relates to a cincturing device for improving male potency by retaining an engorged condition of the male sex organ, such device comprising a ring of elastic material, having a generally circular outside diameter and inside diameter, with a protruding region integrally defined by such ring for receipt of the user's male sex organ urethra; and handle means integrally formed with peripheral portions of such ring for facilitating manipulation and alignment of same. The ring and handle means preferably comprise an integral construction of elastic rubber, so that the ring may be elastically fitted to the base of a user's male sex organ for cincturing blood flow therefrom at peripheral areas of the user's male sex organ so as to retain an engorged condition of such organ, while the user's urethra is received in the protruding region therefor so as to decrease stricture of the urethra for improved discharge of seminal fluids.

Another present exemplary embodiment concerns an improved cincturing device for augmenting male potency by being elastically fitted to the base of a user's male sex organ for cincturing blood flow therefrom at peripheral areas of such organ so as to retain an engorged condition thereof. Such device preferably comprises a combination of a ring with handle means and venous pressure means.

The ring in such embodiment is preferably comprised of relatively elastic material, having a generally circular outside diameter and inside diameter, with a radially outwardly protruding region integrally defined by the ring for receipt of the user's male sex organ urethra so as to decrease stricture thereof for improved discharge of seminal fluids. The handle means are integrally formed with peripheral portions of the ring for facilitating manipulation and alignment of same. The venous pressure means, comprising a pair of radially inwardly protruding regions integrally formed with the ring, are for applying blood flow restrictive forces to the generally dorsal venous process of the user's male sex organ without direct force to the dorsal arterial process or the dorsal neurovascular bundle thereof.

Yet other exemplary constructions comprising present exemplary embodiments relate to apparatus for retaining an engorged condition of the male sex organ when applied about the base of such organ in a predetermined rotational relationship thereto, such an apparatus comprising a cincture band comprised of relatively elastic material having a relatively smooth inside diameter for fitting to the base of the user's male sex organ with a predetermined dorsal band area thereof received adjacent the dorsal region of such organ; and pressure means, comprised of relatively inelastic material received on the cincture band inside diameter on respective sides of the dorsal band area circumferentially displaced therefrom a predetermined distance, for restricting blood egress through the generally dorsal venous process of the user's male sex organ by applying pressure thereto without direct pressure to the center of the organ dorsal region.

Still another present exemplary embodiment is directed to an improved cincturing device for effectively maintaining an engorged condition of the human penis applied to the base thereof with minimized user pressure discomfort or loss of sensation, for improving the potency of a user otherwise unable to adequately sustain penal erection, such device preferably comprising in combination a generally circular ring, a generally U-shaped urethra channel, first and second handle loops, first and second venous pressure regions, and first and second pressure elements.

With the foregoing embodiment, the ring is preferably integrally formed of elastic material with a predetermined inside diameter having a predetermined dorsal ring area for rotational alignment with the corresponding dorsal region of the user's penis. The generally U-shaped urethra channel is defined integrally in the ring radially outward from the inside diameter thereof in a location diametrically opposite to the predetermined dorsal ring area, for receiving a user's urethra for relatively unrestricted discharge of seminal fluid therethrough.

The foregoing first and second handle loops are preferably integrally formed with the outside diameter of the circular ring and project radially outward therefrom at respective positions centered circumferentially about halfway between the predetermined dorsal ring area and the urethra channel. The first and second venous pressure regions are integrally defined with the ring inside diameter and project radially inward therefrom. The venous pressure regions have a curved surface of a predetermined radius located at respective positions centered circumferentially about halfway between the predetermined dorsal ring area and the respective first and second handles. The predetermined radius of the venous pressure regions is greater than at least half the radius of the circular ring predetermined inside diameter. The venous pressure regions further define respective pressure element chambers therein with respective openings thereto.

Still further in such embodiment, the first and second pressure elements are formed of relatively inelastic material and are received in respective chambers of the first and second venous pressure regions. With such arrangement, blood flow restrictive pressure is applied to selected circumferential locations at the base of the user's penis without applying direct pressure to the penis dorsal arterial process or the penis dorsal neurovascular bundle, resulting in effective maintenance of an engorged penal condition with minimized user pressure discomfort or loss of sensation.

Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof, directed to one of ordinary skill in the art, is set forth in the remainder of the specification, which makes reference to the appended figures in which.

Figure 1:
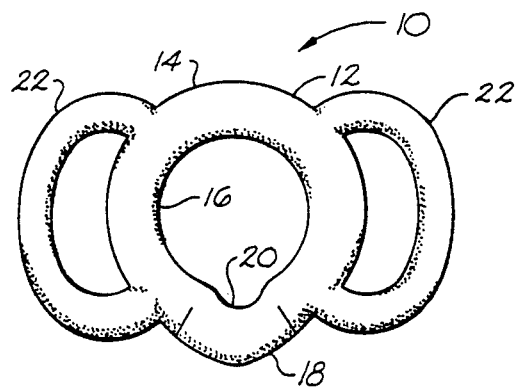
FIG. 1 is a top plan view of an exemplary cincture band device in accordance with one embodiment of the subject invention.

Repeat use of reference characters throughout the present specification and appended drawings is intended to represent same or analogous features or elements of the invention.

DETAILED DESCRIPTION OF THE PREFERRED EMBODIMENTS

Figure 2:
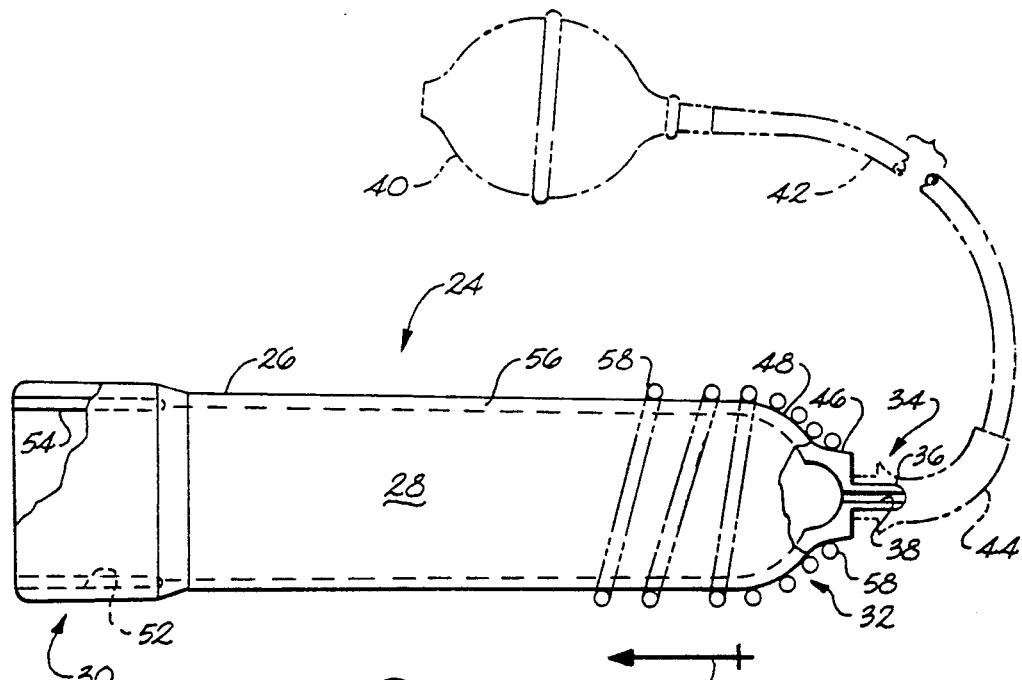
FIG. 2 is a longitudinal cross sectional view of an exemplary cincture band embodiment in accordance with the present invention shown being optionally used in combination with vacuum chamber features.

Those of ordinary skill in the art will appreciate that the following description is by way of example only, and is intended with reference to the exemplary embodiments and configurations illustrated in the present figures. Furthermore, it should be further appreciated that given illustrations of embodiments incorporate various present features which may be otherwise associated with one another in other embodiments of this invention. For example, present FIG. 1 illustrates an embodiment including certain present cincture band features, while FIG. 2 illustrates a combination of cincture band features with vacuum chamber features. Other figures illustrate still further specific examples of present exemplary cincture bands which may be used in conjunction with other aspects of this invention.

Reference will be made throughout this specification to various anatomical features and physiological processes of the male sex organ (i.e., penis), although it is expected that all such features and processes will be well known, and known in detail, to those of ordinary skill in the art. Also, further background on such information is set forth in considerable detail in the above-cited U.S. patents, all of which have been fully incorporated herein by reference.

One of the presently preferred cincture band embodiments is shown in present FIG. 1 and is discussed in greater detail hereinafter.

Exemplary cincturing device 10 as illustrated in FIG. 1 comprises an apparatus for improving male potency by retaining an engorged condition of the male sex organ. Preferably, a ring of elastic material 12 has a generally circular outside diameter 14 and inside diameter 16, with a radially outward protruding region 18 defined thereby. Such protruding region is adapted for receipt of the user's male sex organ urethra in a receiving portion 20 thereof defined in a given circumferential region of inside diameter 16.

Though not specifically illustrated, those of ordinary skill in the art will appreciate that cincturing device 10 may be received about the base of a user's male sex organ with such a rotation and alignment so that the urethra of the user's male sex organ is aligned or received within portion 20 of expanded or protruding region 18. The primary benefit of such arrangement is that there is an improved or greater free discharge of seminal fluids along and from the urethra, or genital duct of the human male, during climactic expulsion. At the same time, the remainder of a properly fitted elastic ring 12 continues to desirably cincture the engorged condition of the male sex organ.

Preferably, a pair of handle means or loops 22 are provided, centered about peripheral positions on diametrically opposite regions of ring 12. Further preferably, such positions are respectively centered about 90 degrees from the center of protruding region 18, thereby providing convenient and functional handles for a user to manipulate ring 12 through introduction of the user's fingers in the respective handles or loops 22.

Still further preferably, such handles 22 may be semi-ellipsoidal, and are integrally formed of elastic material with ring 12. Such handle shape results in improved, more efficient grasping and manipulation of cincturing device 10. The elastic nature of handles 22 also helps the ring 12 to be manually expanded for placement thereof over a flaccid penis. Other methods may be used for expanding ring 12, such as discussed below with reference to present FIG. 2.

Furthermore, it is preferred for some embodiments that the cross section of the circular ring 12 and semi-ellipsoidal handle members 22 be circular (or at least curved). Such prevents the introduction of sharp edges around the male sex organ, and also facilitates manufacture and use of article 10.

It is also preferred that the diameter of handles means 22 be smaller than that of ring 12, so that such handles may be unobtrusive to the extent that they may be received within the open proximal end of a vacuum chamber, such as the exemplary end illustrated to the left in FIG. 2 and discussed below, whereby a "second" vacuum may be effected during use of the male potency apparatus. In other words, a "first" vacuum with a given vacuum chamber results in production of a particular level of male sex organ engorgement, preferably followed by cincturing thereof with a device such as apparatus 10. Thereafter, with a device 10 received on the root of the user's male sex organ, the vacuum chamber is removed therefrom, after which the user may assess the level of engorgement (i.e., penile erection).

If additional erection or firmness is desired, a "second" vacuum may be effected by reintroducing the male sex organ into a vacuum chamber. It is at such time that handles 22 of the FIG. 1 embodiment may be unobtrusively and resiliently bent rearwardly towards the root of the user's male sex organ, or otherwise fitted into the open proximal end of the vacuum chamber to permit a "second" vacuum operation while the cincturing device 10 remains seated on the root of the user's male sex organ. Such an arrangement advantageously permits desired fine tuning or increasing of an initial engorged condition, while keeping in place the cincturing device associated with such first engorged condition or level of engorgement. That is, the erection level once achieved is maintained, rather than lost, while being assessed or treated for enhancement.

Still further, it is generally desired that the diameter of circular ring 12 be somewhat greater than that of the respective handles 22 for the purpose that application of a single such cincturing device 10 may be adequate for retention of an engorged condition of a user s male sex organ. For example, the diameter of circular ring 12 may be in a range of diameters centered about a thickness of 0.6 centimeters (0.24 inches), while the diameter of the respective handle elements 22 is in an exemplary range of diameters centered about a thickness of 0.4 centimeters (0.16 inches). Alternatives may be practiced, and specific further examples are discussed below.

The foregoing functional features, advantages, and aspects of cincturing device 10 are totally apart from aesthetic and ornamental features and appeal of the design otherwise also embodied in device 10. The same is true generally for further cincture band embodiments discussed and illustrated in this application.

It is a still further embodiment of the present invention that a cincturing device 10 as illustrated in present FIG. 1 (or in other figures to follow) may be provided in combination with a vacuum chamber means for producing an engorged condition of a user's male sex organ, for subsequent retention thereof with such elastic or resilient apparatus 10. Vacuum chamber means such as discussed hereinafter with reference to present FIG. 2 may be practiced in such embodiments, or may be substituted by alternative constructions.

FIG. 2 illustrates in side longitudinal cross section one exemplary improved apparatus for augmenting male potency in accordance with the present invention, in use with a vacuum chamber arrangement. A generally cylindrical member 24 has an outside diameter 26 defined by its circumference. Cylindrical member 24 constitutes a vacuum chamber having an interior chamber 28 within which at least a partial negative pressure is created while a user's male sex organ is at least partially received therein, as well understood by those of ordinary skill in the art without more specific illustration (i.e., the positioning of a male appendage as relates to the present apparatus is understood without direct illustration of such).

A proximal longitudinal end 30 of cylindrical member 24 is generally open for passage of a user's male sex organ therethrough into interior chamber 28. Such end 30 is referred to as proximal because it is brought into contact with a user during use of apparatus 24 while an opposite distal end 32 is generally removed from the body (i.e., the torso) of the user. Distal end 32 is generally closed, but may have a passage therethrough defined by vacuum connector means 34 formed therein. Such means 34 may comprise a vacuum connector fitting with a variety of forms, such as an extended stem portion 36 and a central passage 38 therein for the production of negative pressure within chamber 28.

A source of vacuum such as squeeze bulb 40, or virtually any other equivalent means (either power driven or manually actuated) for providing a source of negative pressure, may be interconnected to vacuum connector means 34 via a vacuum hose 42 or the like. Another preferred example is a hand pump device, such as available from Neward Industries of California. Vacuum hose 42 may be connected through a fitting 44 or similar device to vacuum connector means 34. U.S. Pat. No. 4,856,498, the entire disclosure of which is incorporated herein by reference, illustrates exemplary vacuum pump, hose, and coupling features which would serve the desired functions. Furthermore, such arrangements are generally well known to those of ordinary skill in the art, wherefore further details need not be discussed for an adequate understanding of this invention.

As represented in present FIG. 2, distal end 32 may terminate in an end 46 of lesser diameter than outside diameter 26 of vacuum chamber 24. Preferably, for the provision of means integral with vacuum chamber 24 for expanding a cincture band applied thereto, a curved or domed portion 48 is formed between outside diameter 26 and reduced diameter terminus 46. Such cincture band ramp or cincture band expansion means 48 integrally formed with vacuum chamber 24 obviates the need for separate equipment or apparatus for expanding a cincture band for subsequent use.

The foregoing arrangement also advantageously results in automatic application of the expanded cincture band to the outside diameter of vacuum chamber 24, for being further directed therealong (in the direction of arrow 50) towards proximal end 30 for being seated onto the base of a user's male sex organ. Once vacuum inducement operations have resulted in the desired level of male sex organ engorgement, a cincture band received adjacent end 30 (not shown) is ready to be advanced onto the base of the user's male sex organ. Such operation cinctures the organ for retaining the engorged condition thereof. Cincture bands making use of handles or other similar mechanisms may be readily otherwise manipulated from apparatus 24 onto the user's male sex organ, and properly rotatably aligned.

It is well understood by those of ordinary skill in the art that various lubricants, such as petroleum jellies or the like, may be commonly used to facilitate placement and movement of cincture bands (expanded or otherwise) along or onto various surfaces, such as along the length of apparatus 24. Similarly, such lubricants may be used to facilitate enlargement of a cincture band over expansion means 48.

Present FIG. 2 illustrates other alternative features which may be practiced in combination with different cincture bands per the present invention. In particular, the illustrated side plan view cutaway of a vacuum chamber 24 shows incorporation of means 52 associated with open proximal end 30 thereof for receiving a tubular insert 54 therein so as to selectively vary the inside diameter of such open end 30 to accommodate differing needs of a respective user. Insert means 54 may comprise tubular configuration organ adapter means as discussed in commonly assigned U.S. Pat. No. 4,856,498, the entire disclosure of which is incorporated herein by reference.

Apparatus 24, as well as insert means 54 and the like, are preferably formed of optically transparent materials, particularly plastics, with one preferred example of such being Lexan (a polycarbonate). Transparent Plexiglas acrylic plastic is another example. Preferably the thickness of a side wall 56 is approximately one eight of an inch. One to two inches of the proximal end have preferably about 3/16 of an inch thick walls for added strength. While use of various inserts 54 permits changes in the inside diameter of open proximal end 30, such is preferably within a range of one and one-half to two and one-half inches. The overall length of the interior chamber 28 preferably is in a range centered about a nine inch length, and generally within about seven to about twelve inches.

Those of ordinary skill in the art will appreciate that various alternative features, such as insert means 54 may be practiced in various combinations with the foregoing features so as to constitute different exemplary embodiments for use with this invention. Likewise, different forms of means for generating a vacuum source may be practiced as well as alternative fittings or couplings therefor. Similarly, alternative cincture band arrangements herewith may be practiced with various vacuum chamber features, for which reason no one present cincture band embodiment in FIG. 2 is represented to the exclusion of other present cincture band embodiments.

FIG. 2 illustrates a progression of the expansion of an exemplary cincture band 58 in accordance with this invention from where it is first applied to the base region 46 of expansion ramp 48, until it reaches the full outside diameter of side 26 of apparatus 24. As the exemplary cincture band 58 is advanced in the direction of arrow 50 (such as with including the use of lubricants or the like), band 58 becomes expanded from its at rest condition shown in the far right position thereof in present FIG. 2. Band 58 may comprise device 10 of present FIG. 1 or one of the alternative embodiments discussed hereinafter.

Figure 3:
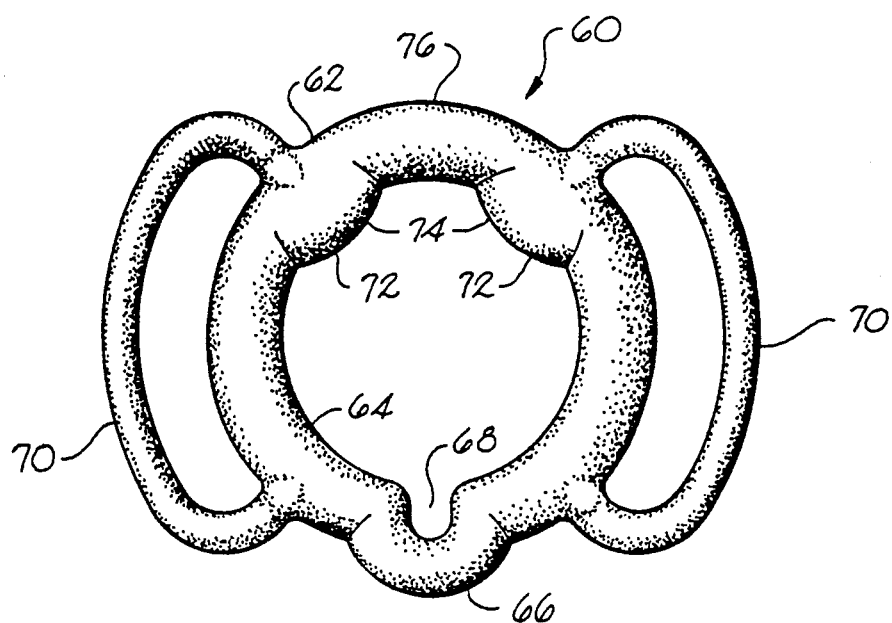
FIG. 3 is top plan view of an exemplary cincture band or ring device in accordance with another embodiment of the subject invention.
Figure 4:
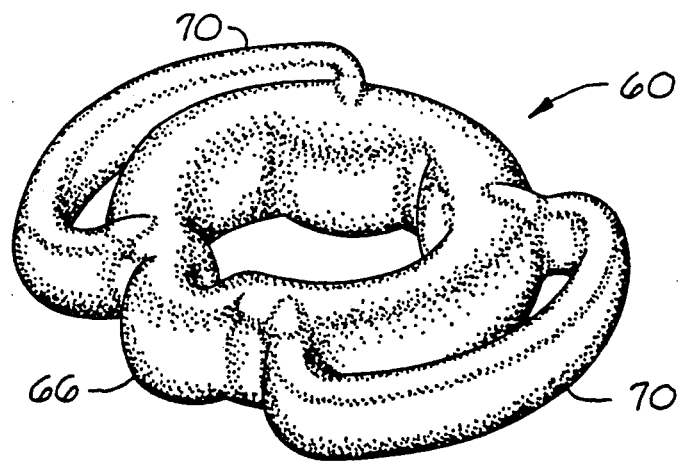
FIG. 4 is a generally side, front perspective view of the exemplary embodiment of FIG. 3.

Present FIGS. 3 and 4 represent a further exemplary cincture device 60 in accordance with the subject invention. More particularly, FIG. 3 illustrates a top plan view of band or ring 60 while FIG. 3 shows a generally side, front perspective view of such device. Similar to the embodiment of present FIG. 1, device 60 may comprise a ring of elastic material having a generally circular outside diameter 62 and relatively smooth inside diameter 64. A protruding region 66 is integrally defined with the ring for receipt of the urethra in region 68. In comparison with present FIG. 1, such urethra receiving region 68 is somewhat more pronounced, and has a more definite U-shaped structure. Functionally, such structure advantageously allows for unrestricted flow of seminal fluid through the urethra during climatic expulsion, when ring 60 is properly seated and rotatably aligned on the base of a user's penis. To facilitate such seating and alignment, handle means 70 are preferably provided, and may comprise at least two loops integrally formed as shown and situated at diametrically opposite sides of ring 60.

A further aspect of the embodiment of FIGS. 3 and 4 relates to enhanced venous pressure means (generally 72) which may be provided on the inside diameter 64 of ring 60. Preferably, such venous pressure means comprise a pair of radially inward protruding regions 74 integrally formed with ring 60 for applying blood flow restrictive forces to the generally dorsal venous process of the penis without direct force to the center of the dorsal region 76. As understood by those of ordinary skill in the art, the penis dorsal region 76 is situated diametrically opposite to the location of the urethra, which is received in channel 68. Just on each lateral side of dorsal region 76 are located subcutaneous lateral veins which are blood flow restricted by properly fitted means 72. However, deep dorsal arteries in region 76 and the dorsal neurovascular bundle beneath such arteries receive no direct pressure from means 72. Therefore, blood flow ingress is maintained and adverse nervous system consequences are avoided with a properly dimensioned and fitted device in accordance with this invention.

While exemplary dimensions are discussed in greater detail below with reference to the embodiment of present FIGS. 5 through 7, FIGS. 3 and 4 are generally drawn to scale so as to illustrate both the positional and relative size relationships of various present features. More particularly, surface stippling is used throughout FIGS. 3 and 4 so as to highlight surface curvatures which contribute to present features of the invention, including effective cincturing of an engorged penis condition with minimized user pressure discomfort or loss of sensation.

More particularly, FIGS. 3 and 4 illustrate that protruding regions 74 comprise curved projections having a first predetermined radius of curvature which intersects with and projects from the ring inside diameter 64. Moreover, such first predetermined radius of curvature is relatively large as compared with the overall ring, by which is meant that the predetermined radius of curvature for regions 74 is generally greater than just about one-half the radius of the ring inside diameter 64. It is to be understood that present reference to the terminology ring inside diameter is not meant to imply that all rings in accordance with the subject invention are perfectly circular, as there may be some oval or elliptic nature for some present embodiments. As will be discussed in greater detail below with several specific dimensional examples, the radius of curvature of regions 74 may in some embodiments be generally greater than at least about two-thirds the radius of the ring inside diameter.

As additionally shown, the respective radii of curvature of such regions preferably are respectively centered about 45 degrees circumferentially around the ring inside diameter 64 from the dorsal centerline of such ring (area 76 generally). As shown, the pair of regions 74 are also formed on respective sides of such centerline. Additional pressure point means which may be enclosed therein as further optional features in accordance with the present invention are discussed in greater detail below with reference to FIGS. 5 through 7.

By providing an embodiment such as in present FIGS. 3 and 4, a relatively smooth inside diameter is presented to the user's penis. With the substantially "gentle" curvature of regions 74 and the highly specific placement thereof relative all remaining features in combination forming the invention, effective blood flow restriction is applied to the superficial and deep dorsal veins in about dorsal region 76 generally. At the same time no direct pressure is applied from regions 74 to the deep dorsal aortic members or the dorsal neurovascular bundle. Such an arrangement permits blood flow ingress by whatever means (for example, from vacuum tumescence enhancement therapy; see present FIG. 2) while also avoiding direct pressure to a major nerve bundle. Hence, such construction further contributes to present objects to avoid loss of sensation to the user, thereby enhancing the overall experience of the therapy.

Figure 5:
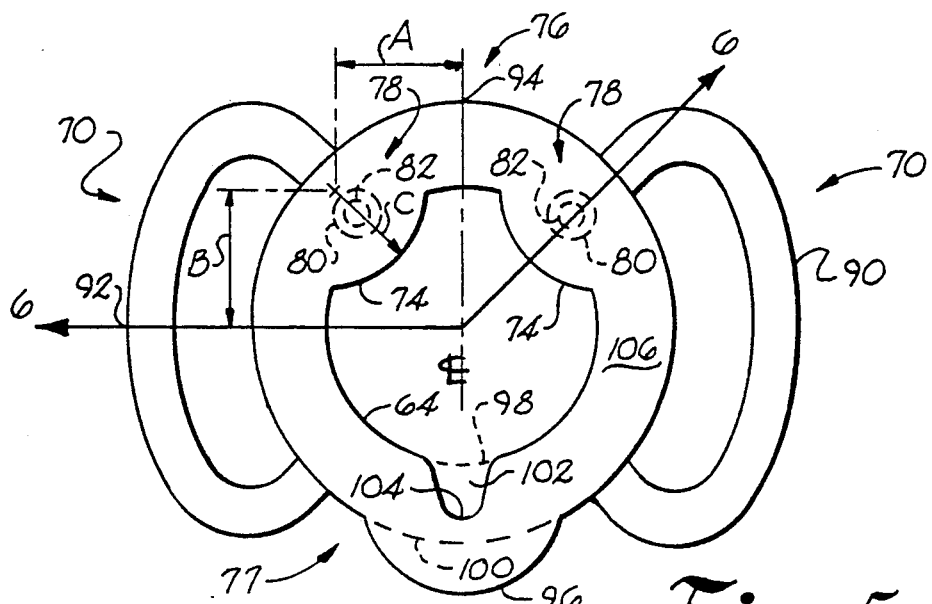
FIG. 5 is a top schematic view of an exemplary cincture band device in accordance with a further embodiment of this invention.
Figure 6:
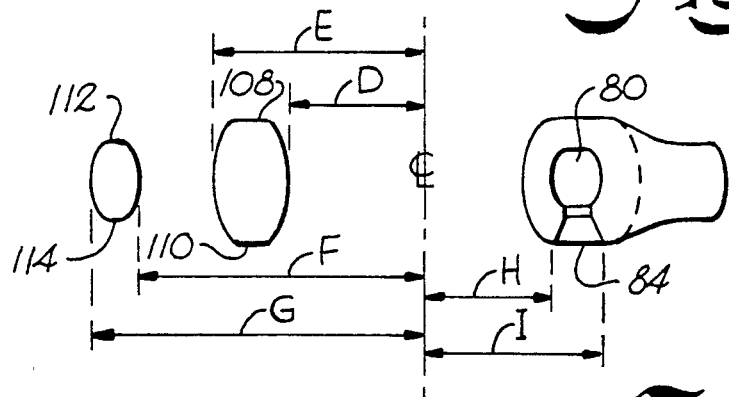
FIG. 6 is a particular cross sectional view taken along the angled cross section line 6—6 of the exemplary embodiment of FIG. 5.
Figure 7:
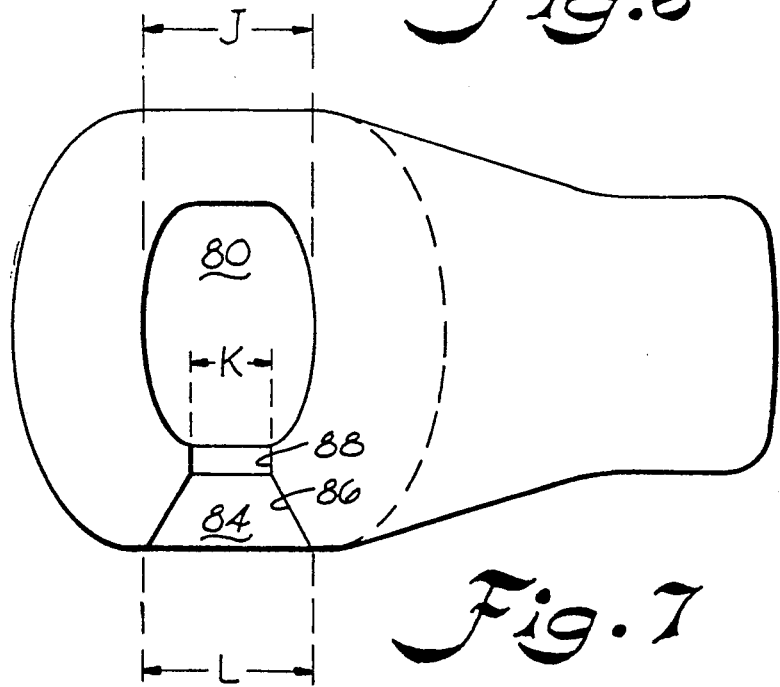
FIG. 7 is an enlarged view of a portion of the sectional view of FIG. 6, showing additional details thereof.

While the present embodiments of FIGS. 3 and 4 may be effective comprising integral constructions of homogenous elastic material such as synthetic rubbers, present FIGS. 5 through 7 illustrate additional optional features of this invention which further contribute to present objects by combining relatively elastic and inelastic materials. More specifically, FIGS. 5 through 7 further illustrate pressure point means in accordance with this invention (generally 78) for enhancing or further increasing venous process blood flow restriction forces applied with the venous pressure means or regions 74. FIG. 5 is a top schematic view of a present embodiment of a ring 77 including such pressure point means features, while FIG. 6 is a particular cross section as indicated by the angled cross section line 6—6 in such FIG. 5 embodiment, and FIG. 7 is an enlargement of a portion of such FIG. 6 cross section.

With reference to such FIGS. 5 through 7, pressure point means 78 may include a receiving chamber 80 formed in each of the inwardly protruding regions 74. In addition, a pressure point element 82 of relatively inelastic material may be received in each of such chambers 80 so as to occupy a predetermined circumferential location relative to the ring inside diameter 64. When occupying such a position, and when ring 77 is properly seated and rotatably aligned, venous process blood flow restrictive forces are projected at desired locations on the user's male sex organ.

As illustrated in present FIGS. 6 and 7, each region 74 may include an opening 84 defined between each of the receiving chambers 80 and the exterior of such regions 74. With such an arrangement the pressure point elements may be introduced through the opening into the respective receiving chamber. As represented in the figures, and as discussed in greater detail below, each such opening 84 may have a predetermined diameter which cooperates with the pressure point elements so as to capture same. Since the openings are defined in regions 74, the material formed therein is relatively elastic. By providing an angled or tapered surface 86 (see FIG. 7), the pressure point elements 82 may be used to progressively and resiliently expand opening 84 beyond an introductory point 88 thereof until gaining access to, and being captured in, chamber 80.

While various pressure point element constructions may be practiced, in presently preferred embodiments such elements may comprise respective spherical members (see 82 of present FIG. 5) having a diameter at least just larger than that of the opening 84 predetermined diameter so as to be retained in the respective receiving chamber 80, as described above.

When considered from another perspective, the exemplary embodiment of present FIGS. 5 through 7 represents a combination of a cincture band 77 comprised of relatively elastic material having a relatively smooth inside diameter 64 with a predetermined dorsal band area 76 thereof received adjacent the dorsal region of a user's male sex organ when band 77 is fitted with the base thereof, combined with pressure means comprised of relatively inelastic material (members 82) received on the cincture band inside diameter 64 on respective sides of such dorsal band area 76 circumferentially displaced therefrom by a predetermined distance. With such arrangement, the pressure means restricts blood egress through the generally dorsal venous process of the penis by applying pressure thereto without direct pressure to the center of the penis dorsal region.

The relatively elastic material may comprise a synthetic rubber material having a Durometer rating of approximately 30 or 31 and a tensile strength generally within a range from about 2200 to about 2400 PSI. Some preferred materials have more specifically a preferred tensile strength of about 2270 to 2275 PSI. The relatively inelastic material may comprise an ABS plastic or other functional equivalents, such as other hardened plastics or in some instances perhaps metallic or composite materials. The combination of the two materials (relatively elastic and inelastic) in such an arrangement beneficially contributes to present objects for providing an effective cincturing device with minimized user pressure discomfort or loss of sensation, all as described above.

As noted above, different present embodiments may include various specific dimensions. In fact, a range of dimensions may be practiced for most present features. The following Table I provides in inches the dimensions of two different exemplary embodiments comprising respectively inside diameters for an unstretched ring of 0.750 inches and 0.875 inches. Reference characters A through L are designated in FIGS. 5 through 7, and will be readily understood and correlated by those of ordinary skill in the art with reference to the following Table I.

TABLE I (All Dimensions in Inches with Reference to FIGS. 5-7)

| | | |
|---|---|---|
| INSIDE DIAMETER OF UNSTRETCHED RING | 0.750 | 0.875 |
| A | .357 | .418 |
| B | .357 | .418 |
| C | .250 | .312 |
| D | .375 | .437 |
| E | .575 | .675 |
| F | .787 | .849 |
| G | .912 | .974 |
| H | .354 | .418 |
| I | .475 | .537 |
| J | .122 | .122 |
| K | .062 | .062 |
| L | .125 | .125 |
| LENGTH (From Outside of Handles) | 1.774 | 1.96 |
| RING WIDTH | 1.150 | 1.40 |
| RING DEPTH | .320 | .320 |
| HANDLE DEPTH | .20 | .20 |
| PRESSURE POINT SPHERE DIAMETER | .135 | .135 |

Those of ordinary skill in the art will further appreciate additional information which may be gained (even without express discussion thereof) from the tabulated examples. For example, the lateral thickness of the ring body of ring 77 may be determined by subtracting the dimension D from the dimension E. Likewise, the thickness of the ring handles may be obtained by subtracting the dimension F from the dimension D.

The length dimension indicated in Table I refers to the length from the outside of the respective diametrically opposite handles 70, i.e., the dimension from between points 90 and 92. The terminology ring width refers to the distance between points 94 and 96. It should be noted from the dotted line representations 98 and 100 of present FIG. 5 that a urethra channel 102 may be optionally included or not included in various present embodiments. When included the depth in a radially outward direction (i.e., the distance between dotted line 98 and channel bottom 104, is preferably greater than at least about 0.1 inches, and more preferably falls in a range of between 0.15 and 0.20 inches. In some preferred embodiments, a specific depth of 0.18 inches may be used for such generally U-shaped channel.

In Table I the terminology ring depth refers to the dimension of the main ring body 106 in the direction perpendicular to the plane of the illustration of present FIG. 5, i.e., the distance between points 108 and 110 of present FIG. 6. Though specific numbers are set forth in the examples of Table I, those of ordinary skill in the art will understand that a range of dimensions may be practiced, for example, in a range generally from about 0.25 to 0.4 inches. The thickness of the handle loops is generally less than that of the ring, in preferred embodiments, as represented in the figures. The terminology handle depth in Table I thus means the dimension of handles 70 in the direction perpendicular to the plane of the illustration of present FIG. 5, i.e., the distance between points 112 and 114 of present FIG. 6. Again, those of ordinary skill in the art will understand that a range of dimensional values may be practiced.

Still further in accordance with the subject invention, an exemplary pressure point sphere diameter may be 0.135 inches, which is greater than the exemplary dimensions J, K, or L of present FIG. 7 (in both embodiments of Table I). As discussed, the relatively inelastic or hard material of the pressure point element progressively enlarges the resilient, tapered surface 86 of opening 84 until passing point 88 so as to become lodged within chamber 80 in a relatively fixed location circumferentially about ring inside diameter 64.

Table I further includes features of the present invention, for example, including information about the radius of curvature C of respective regions 74. With reference to the embodiment of a 0.750 inch diameter embodiment, the ratio of the radius of curvature (dimension C) to the dimension of the radius of the inside diameter (dimension D) for such embodiment is 0.666 or 66.6 percent. In other words, the radius of curvature of the radially projecting regions 74 is greater than at least one-half of the radius of the inside diameter of the ring, and generally about ⅔ of such radius. When looking to the example of the 0.875 inch diameter embodiment, the ratio of dimension C to dimension D is 0.713 or 71.3 percent, still in keeping with the general statements above. By providing such an arrangement, an effective cincturing function is provided, at the same time maximizing relative surfaces for user comfort. In other words, the combination of the radius of curvature of the venous pressure regions 74, together with their circumferential location, i.e., spacing in relation to the dorsal region of the penis, and the size and location of the relative inelastic material supported thereby, forms a highly effective pressure means as described above, notwithstanding the effectiveness of various present embodiments not incorporating specifically the use of a relatively inelastic material.

Various modifications and variations to the foregoing features may be practiced, as alluded to throughout the present specification. For example, in some embodiments, use of a urethra channel and/or use of handles or handles of a specific form and nature, may be varied. Also, use of the relatively inelastic material may be made by forming pressure regions 74 with such materials imbedded therein during manufacture of the ring. In other words, a specific chamber opening may be omitted and the ring regions 74 formed about a sphere or other form of pressure element.

Still further, those of ordinary skill in the art will understand the broader aspects and teachings of the subject invention, which are not expressly limited in all embodiments to specific dimensions, though presently stated dimensions form examples of presently preferred embodiments.

It should be further understood by those of ordinary skill in the art that the foregoing presently preferred embodiments are exemplary only, and that the attendant description thereof is likewise by way of words of example rather than words of limitation, and their use does not preclude inclusion of such modifications, variations, and/or additions to the present invention as would be readily apparent to one of ordinary skill in the art, the scope of the present invention being set forth in the appended claims.

What is claimed is:

1. A cincturing device for improving male potency by retaining an engorged condition of the male sex organ, comprising:
    a ring of elastic material, having a generally circular outside diameter and inside diameter, with a protruding region integrally defined by said ring for receipt of the user's male sex organ urethra; and
    handle means integrally formed with peripheral portions of said ring for facilitating manipulation and alignment of same;
    wherein said ring and said handle means comprise an integral construction of elastic rubber, so that said ring may be elastically fitted to the base of a user's male sex organ for cincturing blood flow therefrom at peripheral areas of the user's male sex organ so as to retain an engorged condition of such organ, while the user's urethra is received in said protruding region therefor so as to decrease stricture of the urethra for improved discharge of seminal fluids.

2. A cincturing device as in claim 1, wherein said handle means comprise a pair of loops disposed respectively on generally diametrically opposite sides of said ring, and respectively centered about 90 degrees from the center of said protruding region.

3. A cincturing device as in claim 1, wherein the thickness of said ring is generally within a range of from about 0.2 inches to 0.4 inches, and wherein such ring thickness is greater than that of said handle means, so that a single such cincturing device is adequate for retention of an engorged condition of a user's male sex organ.

4. A device as in claim 1, further combined with vacuum chamber means for producing an engorged condition of user's male sex organ, for subsequent retention thereof with said elastic ring.

5. A device as in claim 1, wherein said handles are semi-ellipsoidal and said region defined for receipt of the user's urethra is generally U-shaped.

6. A device as in claim 1, further including a pair of inward pressure point projections integrally defined on said ring inside diameter, one each of said projections being located circumferentially between said protruding region and a dorsal ring area defined on said ring diametrically opposite to said protruding region thereof.

7. A device as in claim 6, wherein each of said projections has a relatively large radius of curvature in relation to said ring inside diameter, has a center point located about 45 degrees circumferentially around said ring from said dorsal ring area, and includes therein a pressure point element formed of relatively inelastic material for augmenting local pressure applied from such projection to the user's male sex organ.

8. A cincturing device for improving male potency by being elastically fitted to the base of a user's male sex organ for cincturing blood flow therefrom at peripheral areas of such organ so as to retain an engorged condition thereof, said device comprising:
    a ring of relatively elastic material, having a generally circular outside diameter and inside diameter, with a radially outwardly protruding region integrally defined by said ring for receipt of the user's male sex organ urethra so as to decrease stricture thereof for improved discharge of seminal fluids;
    handle means integrally formed with peripheral portions of said ring for facilitating manipulation and alignment of same; and
    venous pressure means, comprising a pair of radially inwardly protruding regions integrally formed with said ring, for applying blood flow restrictive forces to the generally dorsal venous process of the user's male sex organ without direct force to the dorsal arterial process or the dorsal neurovascular bundle thereof;
    wherein said pair of inwardly protruding regions comprise curved projections having a first predetermined radius of curvature intersecting with and projecting from said ring inside diameter;
    wherein said first predetermined radius of curvature is generally greater than at least one-half the radius of said ring inside diameter; and
    wherein said inwardly protruding regions further include associated therewith pressure point means for further increasing venous process restrictive forces applied with said venous pressure means.

9. A cincturing device as in claim 8, wherein said first predetermined radius of curvature is relatively large compared with said ring.

10. A cincturing device as in claim 8, wherein said first predetermined radius of curvature is generally greater than at least about two-thirds the radius of said ring inside diameter.

11. A cincturing device as in claim 8, wherein said inwardly protruding regions are respectively centered about 45 degrees circumferentially around said ring inside diameter from the dorsal centerline of said ring, and on respective sides thereof.

12. A cincturing device as in claim 8, wherein said pressure point means includes a receiving chamber formed in each of said inwardly protruding regions, and a pressure point element of relatively inelastic material received in each of said chambers so as to occupy a predetermined circumferential location relative said ring inside diameter so that such increased venous process restrictive forces are projected at desired locations on the user's male sex organ.

13. A cincturing device as in claim 12, further including an opening defined between each of said receiving chambers and the exterior of its respective inwardly protruding region, through which each of said pressure point elements may be introduced into its respective receiving chamber.

14. A cincturing device as in claim 13, wherein said openings have a predetermined diameter and said pressure point elements comprise spherical members having a diameter at least just larger than that of said opening predetermined diameter so as to be retained in its respective receiving chamber.

15. A cincturing device as in claim 14, wherein:
said ring inside diameter is generally within a range from about 0.7 to about 0.9 inches;
the thickness of said ring is generally within a range from about 0.25 to 0.4 inches; and
said relatively elastic material has a Durometer rating of about 30 and a tensile strength generally within a range from about 2200 to about 2400 PSI.

16. Apparatus for retaining an engorged condition of the male sex organ when applied about the base of such organ in a predetermined rotational relationship thereto, said apparatus comprising:
a cincture band comprised of relatively elastic material having a relatively smooth inside diameter for fitting to the base of the user's male sex organ with a predetermined dorsal band area thereof received adjacent the dorsal region of such organ; and
pressure means, comprised of relatively inelastic material received on said cincture band inside diameter on respective sides of said dorsal band area circumferentially displaced therefrom a predetermined distance, for restricting blood egress through the generally dorsal venous process of the user's male sex organ by applying pressure thereto without direct pressure to the center of the organ dorsal region.

17. An apparatus as in claim 16, wherein said pressure means includes a radially inwardly projection formed integrally with said cincture band on each respective side of said dorsal band area thereof, and a pressure element received in each of said inwardly directed projections.

18. An apparatus as in claim 17, wherein each of said projections has a predetermined radius of curvature which is centered at a point displaced about 45 degrees from the center of said dorsal band area.

19. An apparatus as in claim 18, wherein said predetermined radius of curvature is greater than at least about one-half of the radius of said cincture band inside diameter.

20. An apparatus as in claim 17, wherein each of said inwardly directed projections defines a chamber therein for receipt of said pressure element in a relatively fixed location therein and further defines an opening to said chamber for introduction of said pressure element thereto.

21. An apparatus as in claim 20, wherein said opening has a predetermined diameter, and said pressure element has a minimum size at least slightly larger than said opening predetermined diameter, so as to be retained in its respective chamber.

22. An apparatus as in claim 21, wherein said pressure element comprises a spherical element of relatively hard plastic material, and said opening is tapered so as to be progressively and resiliently expanded in an enlarging direction as said pressure element is introduced into the respective chamber through such opening.

23. An apparatus as in claim 16, further including handle means integrally formed with said cincture band for manipulating and aligning same.

24. An apparatus as in claim 23, further including an outwardly directed projection defined in said cincture band in a circumferential location thereof generally opposite to that of said dorsal band area, and forming a channel for receiving the urethra of the user's male sex organ.

25. An apparatus as in claim 24, wherein said handle means comprise at least two loops directed radially outward from the outside diameter of said cincture band.

26. An apparatus as in claim 25, wherein said loops are formed on diametrically opposite sides of said cincture band, and are located circumferentially about halfway between said dorsal band area and said outwardly directed projection.

27. An improved cincturing device for effectively maintaining an engorged condition of the human penis applied to the base thereof with minimized user pressure discomfort or loss of sensation, for improving the potency of a user otherwise unable to adequately sustain penal erection, said device comprising:
a generally circular ring integrally formed of elastic material with a predetermined inside diameter having a predetermined dorsal ring area for rotational alignment with the corresponding dorsal region of the user's penis;
a generally U-shaped urethra channel defined integrally in said ring radially outward from said inside diameter thereof in a location diametrically opposite to said predetermined dorsal ring area, for receiving a user's urethra for relatively unrestricted discharge of seminal fluid therethrough;
first and second handle loops integrally formed with the outside diameter of said circular ring and projecting radially outward therefrom at respective positions centered circumferentially about halfway between said predetermined dorsal ring area and said urethra channel;
first and second venous pressure regions integrally defined with said ring inside diameter and projecting radially inward therefrom, said venous pressure regions having a curved surface of a predetermined radius located at respective positions centered circumferentially about halfway between said predetermined dorsal ring area and said respective first and second handles, said predetermined radius of said venous pressure regions being greater than at least half the radius of said circular ring predetermined inside diameter, said venous pressure regions further defining respective pressure element chambers therein with respective openings thereto; and
first and second pressure elements formed of relatively inelastic material and received in respective chambers of said first and second venous pressure regions, so that blood flow restrictive pressure is applied to selected circumferential locations at the base of the user's penis without applying direct pressure to the penis dorsal arterial process or the penis dorsal neurovascular bundle, resulting in effective maintenance of an engorged penal condition with minimized user pressure discomfort or loss of sensation.

28. An improved cincturing device as in claim 27, wherein the radius of said ring inside diameter is greater than at least about 0.3 inches, the thickness of said ring is at least about 0.2 inches, and said pressure elements comprise respective spherical elements having a diameter of at least about 0.1 inches.

29. An improved cincturing device as in claim 28, wherein the inside diameter of said ring is generally from about 0.7 to 0.9 inches, the thickness of said ring is generally from about 0.25 to 0.4 inches, the thickness of said handle loops is generally less than that of said ring, and the radially outward depth of said U-shaped urethra channel is at least about 0.1 inches.

30. An improved cincturing device as in claim 29, wherein said ring inside diameter is generally about 0.75 inches, the thickness of said ring is generally from about 0.30 to 0.35 inches, the thickness of said handle loops is generally less than 0.25 inches, and the radially outward depth of said U-shaped urethra channel is generally from about 0.15 to 0.20 inches.

31. An improved cincturing device as in claim 29, wherein said ring inside diameter is generally about 0.875 inches, the thickness of said ring is generally from about 0.30 to 0.35 inches, the thickness of said handle loops is generally less than 0.25 inches, and the radially outward depth of said U-shaped urethra channel is generally from about 0.15 to 0.20 inches.

32. A cincturing device for improving male potency by retaining an engorged condition of the male sex organ, comprising:

a ring of elastic material, having a generally circular outside diameter and inside diameter, with a protruding region integrally defined by said ring for receipt of the user's male sex organ urethra; and handle means integrally formed with peripheral portions of said ring for facilitating manipulation and alignment of same;

wherein said ring and said handle means comprise an integral construction of elastic rubber, so that said ring may be elastically fitted to the base of a user's male sex organ for cincturing blood flow therefrom at peripheral areas of the user's male sex organ so as to retain an engorged condition of such organ, while the user's urethra is received in said protruding region therefor so as to decrease stricture of the urethra for improved discharge of seminal fluids; and said device further including a pair of inward pressure point projections integrally defined on said ring inside diameter, one each of said projections being located circumferentially between said protruding region and a dorsal ring area defined on said ring diametrically opposite to said protruding region thereof; and wherein each of said projections has a relatively large radius of curvature in relation to said ring inside diameter, has a center point located about 45 degrees circumferentially around said ring from said dorsal ring area, and includes therein a pressure point element formed of relatively inelastic material for augmenting local pressure applied from such projection to the user's male sex organ.

* * * * *